US010071216B2

(12) United States Patent
Rutan

(10) Patent No.: US 10,071,216 B2
(45) Date of Patent: Sep. 11, 2018

(54) LINER FOR USE WITH RESPIRATORY MASK

(71) Applicant: Naturs Design, Inc., Jackson, MI (US)

(72) Inventor: Robert M. Rutan, Jackson, MI (US)

(73) Assignee: Naturs Design, Inc., Jackson, MI (US)

( * ) Notice: Subject to any disclaimer, the term of this patent is extended or adjusted under 35 U.S.C. 154(b) by 403 days.

(21) Appl. No.: 14/831,371

(22) Filed: Aug. 20, 2015

(65) Prior Publication Data

US 2015/0352307 A1 Dec. 10, 2015

Related U.S. Application Data

(63) Continuation-in-part of application No. 13/758,783, filed on Feb. 4, 2013, now Pat. No. 9,113,667, which is a continuation-in-part of application No. 12/469,998, filed on May 21, 2009, now Pat. No. 8,365,733.

(60) Provisional application No. 61/056,893, filed on May 29, 2008.

(51) Int. Cl.
*A61M 16/06* (2006.01)
*A62B 18/08* (2006.01)
*A61B 5/097* (2006.01)

(52) U.S. Cl.
CPC ............. *A61M 16/06* (2013.01); *A61B 5/097* (2013.01); *A61M 16/0622* (2014.02); *A61M 16/0666* (2013.01); *A62B 18/08* (2013.01); *A61M 16/0605* (2014.02); *A61M 16/0633* (2014.02); *A61M 16/0683* (2013.01); *A61M 2205/0205* (2013.01); *A61M 2205/0216* (2013.01); *A61M 2205/0238* (2013.01)

(58) Field of Classification Search
CPC .......... A61M 16/0605; A61M 16/0616; A61M 16/0622; A61M 16/0666; A61M 16/0683; A61M 16/0688
See application file for complete search history.

(56) References Cited

U.S. PATENT DOCUMENTS

| 1,990,199 A | 2/1935 | Nemzek |
| 2,008,677 A | 7/1935 | Booharin |
| 2,435,721 A | 2/1948 | Lehmann |
| 2,931,356 A | 4/1960 | Schwartz |

(Continued)

FOREIGN PATENT DOCUMENTS

| CN | 1681551 A | 10/2005 |
| CN | 1681553 A | 10/2005 |

(Continued)

OTHER PUBLICATIONS

International Search Report and Written Opinion for corresponding Application No. PCT/US2016/047121, dated Nov. 17, 2016, 11 pages.

(Continued)

*Primary Examiner* — Lynne Anderson
(74) *Attorney, Agent, or Firm* — Brooks Kushman P.C.

(57) ABSTRACT

A liner for use with a respiratory mask having a frame portion which is detachable from a cushion portion is provided, the liner including a body constructed from an absorbent material, the body having a first end and a second end, the body including a hose aperture adjacent the first end and sized for placement over a hose connector of the respiratory mask, and a mouth aperture adjacent the second end for placement over a mouth opening of the mask to allow air to flow into a user's mouth.

19 Claims, 13 Drawing Sheets

(56) References Cited

U.S. PATENT DOCUMENTS

| | | |
|---|---|---|
| 3,130,722 A | 4/1964 | Etal |
| 3,357,426 A | 12/1967 | Cohen |
| 4,069,516 A | 1/1978 | Watkins, Jr. |
| D257,063 S | 9/1980 | Galindo |
| 4,856,508 A | 8/1989 | Tayebi |
| 5,003,633 A | 4/1991 | Itoh |
| 5,146,914 A | 9/1992 | Sturrock |
| 5,243,971 A | 9/1993 | Sullivan et al. |
| 5,921,239 A | 7/1999 | McCall et al. |
| 6,016,805 A | 1/2000 | Burns et al. |
| 6,082,360 A | 7/2000 | Rudolph et al. |
| 6,196,223 B1 | 3/2001 | Belfer et al. |
| D442,352 S | 5/2001 | Benjamin et al. |
| 6,338,340 B1 | 1/2002 | Finch et al. |
| 6,468,222 B1 | 10/2002 | Mault et al. |
| 6,629,531 B2 | 10/2003 | Gleason et al. |
| 6,698,427 B1 | 3/2004 | Clowers |
| 6,698,727 B1 | 3/2004 | Shaw |
| 6,851,429 B2 | 2/2005 | Bishop |
| 6,926,004 B2 | 8/2005 | Schumacher |
| 6,955,650 B2 | 10/2005 | Mault et al. |
| 7,000,614 B2 | 2/2006 | Lang et al. |
| 7,017,577 B2 | 3/2006 | Matich |
| 7,077,138 B2 | 7/2006 | Bateman et al. |
| 7,178,525 B2 | 2/2007 | Matula, Jr. et al. |
| 7,219,670 B2 | 5/2007 | Jones, Jr. et al. |
| 7,234,466 B2 | 6/2007 | Kwok et al. |
| 7,243,650 B2 | 7/2007 | Thornton |
| 7,296,574 B2 | 11/2007 | Ho et al. |
| 7,370,652 B2 | 5/2008 | Matula, Jr. et al. |
| 7,427,703 B2 | 9/2008 | Geier |
| D644,729 S | 9/2011 | Ferris et al. |
| 8,171,934 B1 | 5/2012 | Ho |
| 8,365,733 B2 | 2/2013 | Rutan |
| D717,939 S | 11/2014 | Koehler |
| D735,318 S | 7/2015 | Roblin-Lee |
| D738,514 S | 9/2015 | Tagami et al. |
| D755,951 S | 5/2016 | Roblin-Sharp |
| 2003/0023182 A1 | 1/2003 | Mault et al. |
| 2004/0194784 A1 | 10/2004 | Bertrand |
| 2004/0244799 A1 | 12/2004 | Landis |
| 2004/0244804 A1 | 12/2004 | Olsen et al. |
| 2004/0261797 A1 | 12/2004 | White et al. |
| 2005/0199239 A1 | 9/2005 | Lang et al. |
| 2005/0268907 A1 | 12/2005 | McFarlane |
| 2005/0279367 A1 | 12/2005 | Klemperer |
| 2005/0284481 A1 | 12/2005 | Meyer et al. |
| 2006/0060200 A1 | 3/2006 | Ho et al. |
| 2006/0081251 A1 | 4/2006 | Hernandez et al. |
| 2006/0107431 A1 | 5/2006 | Curran et al. |
| 2006/0130845 A1 | 6/2006 | Schegerin |
| 2006/0144399 A1 | 7/2006 | Davidowski et al. |
| 2006/0283452 A1 | 12/2006 | Woodard et al. |
| 2007/0006879 A1 | 1/2007 | Thornton |
| 2007/0017525 A1 | 1/2007 | Madaus et al. |
| 2007/0050883 A1 | 3/2007 | Matich |
| 2007/0157934 A1 | 7/2007 | Lang et al. |
| 2007/0175479 A1 | 8/2007 | Groll |
| 2007/0175480 A1 | 8/2007 | Gradon et al. |
| 2008/0047560 A1 | 2/2008 | Veliss et al. |
| 2008/0110469 A1 | 5/2008 | Weinberg |
| 2008/0127984 A1 | 6/2008 | Thornton |
| 2008/0257354 A1 | 10/2008 | Davidson et al. |
| 2008/0302365 A1 | 12/2008 | Cohen et al. |
| 2009/0050144 A1 | 2/2009 | Pierce et al. |
| 2009/0107507 A1 | 4/2009 | Moore |
| 2009/0139525 A1 | 6/2009 | Schirm |
| 2009/0211581 A1 | 8/2009 | Bansal |
| 2009/0293880 A1 | 12/2009 | Rutan |
| 2010/0031958 A1 | 2/2010 | Stewart |
| 2010/0326445 A1 | 12/2010 | Veliss et al. |
| 2011/0005524 A1 | 1/2011 | Veliss et al. |
| 2011/0061656 A1 | 3/2011 | Matich |
| 2011/0226240 A1 | 9/2011 | Navalesi et al. |
| 2012/0080035 A1 | 4/2012 | Guney et al. |
| 2012/0180795 A1 | 7/2012 | Knight |
| 2012/0204881 A1 | 8/2012 | Davidson et al. |
| 2013/0139290 A1 | 6/2013 | Barski |
| 2013/0139829 A1 | 6/2013 | Rutan |
| 2014/0150799 A1 | 6/2014 | Daly |
| 2014/0190492 A1 | 7/2014 | Noh et al. |
| 2014/0345621 A1 | 11/2014 | Zack et al. |
| 2015/0352309 A1 | 12/2015 | Daly |
| 2015/0374943 A1 | 12/2015 | Alexani |
| 2015/0374945 A1 | 12/2015 | Anthony |
| 2016/0279359 A1 | 9/2016 | Chang et al. |
| 2016/0339196 A1 | 11/2016 | Bowsher |
| 2017/0049983 A1 | 2/2017 | Ellis |

FOREIGN PATENT DOCUMENTS

| | | |
|---|---|---|
| CN | 101653632 A | 2/2010 |
| CN | 102065786 A | 5/2011 |
| CN | 102448550 A | 5/2012 |
| GB | 162526 A | 5/1921 |
| JP | 4420956 | 9/1969 |
| JP | S4420956 | 9/1969 |
| JP | S05014702 | 5/1975 |
| JP | 61185446 | 11/1986 |
| JP | S61185446 | 11/1986 |
| JP | 05051364 U | 7/1993 |
| JP | 2000217940 | 8/2000 |
| JP | 2003501220 A | 1/2003 |
| JP | 2003052845 | 2/2003 |
| JP | 2003052845 A | 2/2003 |
| JP | 2005537904 A | 12/2005 |
| KR | 20100003822 A | 1/2010 |
| WO | 99925410 | 5/1999 |
| WO | 200050121 | 8/2000 |
| WO | 0076568 | 12/2000 |
| WO | 2004022145 A1 | 3/2004 |
| WO | 2008011683 | 1/2008 |
| WO | 2008137644 A1 | 11/2008 |
| WO | 2014120492 A1 | 8/2014 |

OTHER PUBLICATIONS

European Search Report for corresponding Application No. 14746739. 3-1662, dated Aug. 17, 2016, 9 pages.
Chinese Office Action and English translation for corresponding Application No. 201480017575.2, dated Sep. 1, 2016, 16 pages.
www.cpaptalk.com, May 6, 2005-Nov. 30, 2005.
International Search Report for the corresponding International Application No. PCT/US2009/045256 dated Jul. 20, 2009.
International Preliminary Report on Patentability and Written Opinion for PCT/US2009/045256 dated Dec. 9, 2010.
Japanese Patent and Trademark Office, Notice of Rejection for Japanese Patent Application No. 2011-511770 dated Jul. 22, 2014.
English Summary of Notice of Rejection for Japanese Patent Application No. 2011-511770 dated Jul. 22, 2014.
Korean Intellectual Property Office, International Search Report and the Written Opinion for the corresponding International Application No. PCT/US2014/012163 dated May 7, 2014.
"Mirage Micro Nasal Mask", ResMed, 2007, from www.resmed. com.
(2006), CPAP Community—View Topic—Mask Gasket [Web log post]. Retrieved from http://www.cpaptalk.com/viewtopic.
(2006), CPAP Community—View Topic—Mask Experiment Success [Web log post]. Retrieved from http://www.cpaptalk.com/viewtopic.
(2005-2011), CPAP Community—View Topic—Directions for Toilet Seat Covering [Web log post]. Retrieved from http://www.cpaptalk.com/viewtopic.
"Pad a Cheek", PAC_OptiLife, from http://www.padacheek.com/PAC_Maskliner.html, obtained from www.archive.org, published at least as early as Apr. 8, 2012.
(Nov. 22, 2007), CPAP Community, "Deconstructed Aura" [Web log post]. Retrieved from http://www.cpaptalk.com/viewtopic.
(2007), CPAP Community, "Decapitating a Twilite NP Mask" [Web log post]. Retrieved from http://cpaptalk.com/viewtopic.

(56) References Cited

OTHER PUBLICATIONS (2007), CPAP Community, by Wulfman [Web log post]. Retrieved from http://cpaptalk.com/viewtopic.
(Nov. 30, 2007), CPAP Community, "what is wrong with me" [Web log post]. Retrieved from http://www.cpaptalk.com/viewtopic.
(Dec. 12, 2008), CPAP Community, "Any one tried a mask cover-gasket" [Web log post]. Retrieved from http://www.cpaptalk.com/viewtopic.
(2005), CPAP Community, "As long as I don't wake up" [Web log post]. Retrieved from http://www.cpaptalk.com/viewtopic.
European Search Report for Application No. 09755675.7, dated Nov. 16, 2017, 10 pages.

LINER FOR USE WITH RESPIRATORY MASK

CROSS-REFERENCE TO RELATED APPLICATIONS

This application is a continuation-in-part of U.S. application Ser. No. 13/758,783 filed Feb. 4, 2013, now U.S. Pat. No. 9,113,667, which is a continuation-in-part of U.S. application Ser. No. 12/469,998 filed May 21, 2009, now U.S. Pat. No. 8,365,733, which, in turn, claims the benefit of U.S. provisional Application No. 61/056,893 filed May 29, 2008, the disclosures of which are incorporated in their entirety by reference herein.

TECHNICAL FIELD

Embodiments relate to a liner for use with a respiratory mask, such as a CPAP mask.

BACKGROUND

Obstructive sleep apnea is a serious and potentially fatal medical condition in which a person's airway becomes physically blocked multiple times during sleep, restricting oxygen intake and causing the person to awake gasping for breath. Possible effects of the condition include extreme fatigue, high blood pressure, strokes, heart attacks, and sometimes even death.

One of the most common treatments of obstructive sleep apnea is the use of a continuous positive airway pressure (CPAP) machine. These machines deliver a continuous flow of pressurized air to the airway through a hose and mask fitted to the face. Patient compliance is a major problem with CPAP users, however, due to discomfort, air leaks, and general ineffectiveness. It is estimated that up to 50% of users discontinue use.

Most CPAP masks currently available are made from silicone, rubber, vinyl, or a nylon-based fabric. These materials are typically water and gas impermeable, which can block off pores, cause sweating, and create pressure marks on the face, increasing the discomfort of the mask. Furthermore, most mask manufacturers recommend against the use of skin or face cream with CPAP masks since the mask material directly contacts the skin. This is a problem for many users, especially those that have dry skin and depend on night cream for skin care.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

One or more embodiments disclosed herein provide an accessory capable of improving the comfort, effectiveness, and/or patient compliance of CPAP and other respiratory masks.

Figure 1:
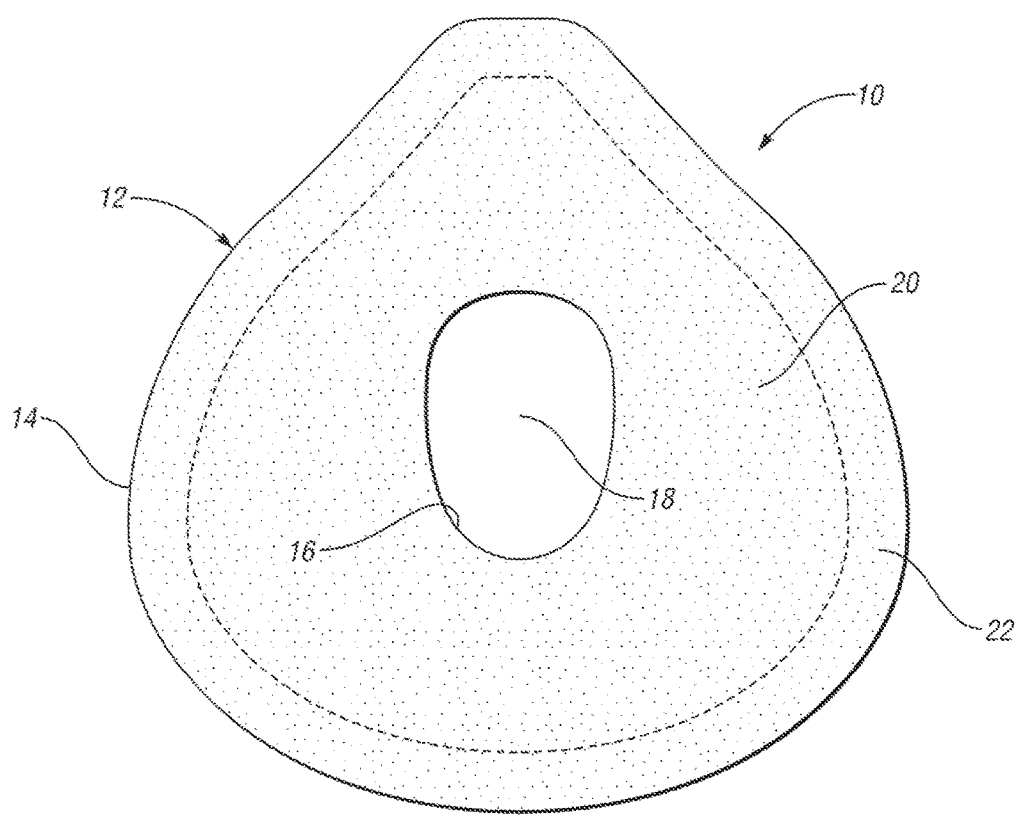
FIG. 1 is a top plan view of a liner according to an embodiment, such as for use with a full-face respiratory mask.
Figure 2:
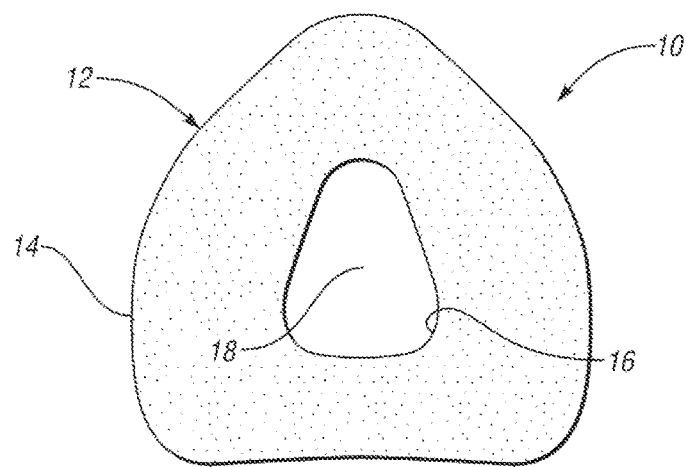
FIG. 2 is a top plan view of a liner according to an embodiment, such as for use with a nasal respiratory mask.
Figure 3:
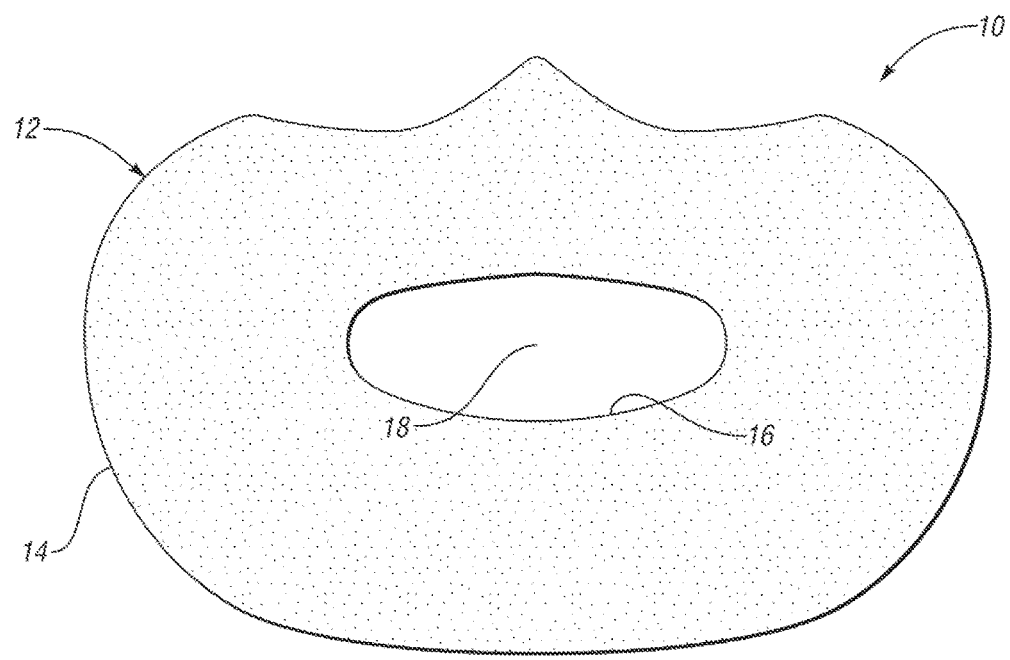
FIG. 3 is a top plan view of a liner according to an embodiment, such as for use with a partial-face respiratory mask.

With reference to FIGS. 1-3, a liner for use with a respiratory mask, such as a CPAP mask M (see FIG. 5), is illustrated and designated generally by reference numeral 10. In use, the liner 10 may be positioned between and held in place by the respiratory mask and the face of a user in order to absorb moisture, maintain proper positioning of the mask M, and greatly reduce or eliminate air from leaking between the mask M and the user's face. Although the liner 10 is described herein primarily in relation to use with a CPAP mask, it is understood that the liner 10 may also be used with other types of respiratory masks such as, but not limited to, oxygen masks, respirators, and filtering masks.

In one embodiment, the liner 10 includes a body 12 having an outer edge 14, an inner edge 16, and an opening 18 bounded by the inner edge 16. The body 12 may be generally oval-shaped, elliptical, round, or triangular, or have any other shape appropriate for use with a respiratory mask, and is not limited to those shapes depicted herein. The opening 18 is configured to at least partially receive the nose, mouth, or both nose and mouth, depending upon the type of mask, allowing air flow from an air source to be received by the user through the mask M. The opening 18 may be generally elliptical or oval-shaped as shown, but is not intended to be limited to these shapes.

Figure 5:
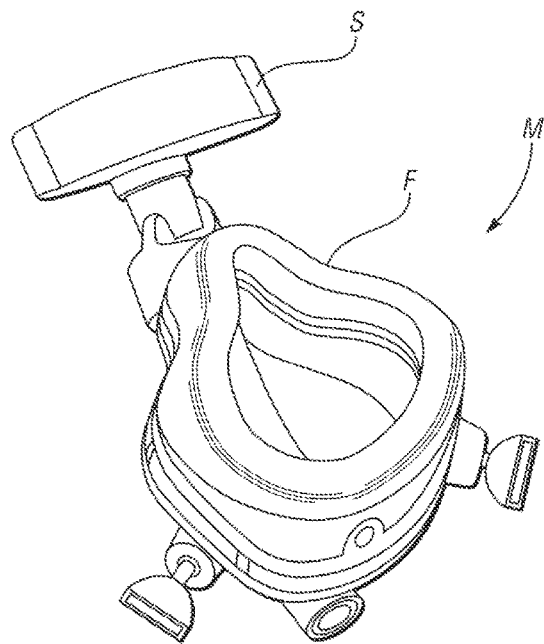
FIG. 5 is a perspective view of an exemplary full-face respiratory mask.

Referring to FIGS. 1 and 5, the outer edge 14 of liner 10 may have a shape scaled to a general shape of a face-engaging portion F of the respiratory mask M. As best shown in FIGS. 6-10, a perimeter of the liner outer edge 14, which may be continuous or discontinuous, is larger than a perimeter of the face-engaging portion F, wherein the liner 10 is configured to be releasably held between the mask M and a user's face such that the outer edge 14 extends beyond the mask face-engaging portion F around at least part of its perimeter. As such, as illustrated in an exemplary manner in FIG. 1, the body 12 has a first portion 20 inward of the perimeter of the face-engaging portion F and a second, extending portion 22 outward of the perimeter of the face-engaging portion F. The extending portion 22 extends outwardly from the face-engaging portion F, and may generally follow the contours of the user's face. Thus, when the liner 10 is releasably held by the mask M and the user's face, the outer edge 14 is spaced apart from the mask M.

In one embodiment, the outer edge 14 may extend beyond the perimeter of the mask face-engaging portion F by between about 0.25 to 1.0 inches, or more particularly may extend between about 0.5 and 0.75 inches. In general, the area of the extending portion 22 may comprise at least about 5%, 10%, or 15% of the area of the body 12, but larger proportions of area represented by the extending portion 22 are also contemplated. By allowing the outer edge 14 of the liner 10 to loosely protrude beyond the mask M, the extending portion 22 is configured to be in non-adhering communication with a user's face and serves to reduce air leaks from the perimeter of the mask M by acting as a baffle to regulate, limit, or diffuse air flow between the mask M and the skin, thus also stopping any resulting squealing-type noises created by such air leaks.

According to an embodiment, the body 12 is constructed from a single layer of absorbent material, wherein the thickness of the body 12 may be between about 0.005 to 0.05 inches, although these dimensions are not intended to be limiting. In one embodiment, the material may include cotton. In another embodiment, the material may include another material, such as silicone, with cotton embedded therein. However, it is understood that any material with suitable absorption and comfort properties may be used. In further accordance with an embodiment, the material used for the construction of the body 12 may be stretchable to aid in adjusting and customizing the fit of the liner 10 to a particular user as described below. The absorbent material may function to absorb moisture and/or oils from the user's skin and enable the mask M to maintain a consistent and comfortable position with respect to the user's face when in use.

In a CPAP system, an air source (not shown) delivers a constant flow of pressurized and humidified air to the CPAP mask M. Due to the moisture of the humidified air, facial perspiration (such as due to contact with the mask material), and oil from the skin, the mask M may slip on the user's face, thus leaking air and awakening the user during sleep. The liner 10 may absorb such moisture and wick it away from the face and mask surfaces. As a result, proper positioning of the mask M with respect to the skin may be maintained, thus eliminating or greatly reducing air leaks and facilitating the ability for a user to wear their CPAP mask successfully throughout the night.

The single layer construction of the liner 10 may act as a sort of "second skin" upon the user's face. As such, the liner 10 is able to provide its baffle function without detracting from the prescribed fit of the mask M since the liner 10 does not appreciably alter the distance of the face-engaging portion F from the user's face. Pressure markings from the mask M may also be reduced or eliminated by use of the liner 10. Furthermore, the absorbent liner material may make use of facial creams possible while wearing the mask M, since direct contact of the skin with the mask material is avoided.

According to an embodiment, the liner 10 is held in place by the pressure of the respiratory mask M upon the face (e.g., by straps around the head). While it is contemplated that the liner 10 could be at least partially fastened to the mask M, advantageously neither elastic nor another mechanism for securing the liner 10 to the mask M is required, allowing for ease of use and manufacture. The position of the liner 10 can be adjusted if necessary while the mask M is secured, and the liner 10 is easily removable and replaceable when the mask M is removed.

Respiratory masks, more particularly CPAP masks, are offered in various shapes and sizes, including full-face, nasal, child-sized, and partial-face (hybrid) configurations. Full-face masks typically include a wider bottom region for covering the mouth area and a narrower upper region for covering the nasal area. Nasal masks generally cover the nasal area and not the mouth area. Child-sized masks may have a proportionally smaller size. Partial-face (hybrid) masks generally cover the mouth and may include a nasal interface. It is therefore contemplated that the outer edge 14 of liner 10 may have a shape similar to a general shape of the face-engaging portion F for a selected mask M, wherein the shape of the outer edge 14 may represent a scaled version of the general shape of the face-engaging portion F.

If the liner 10 is to be used with a full-face CPAP mask, the opening 18 may be sized to at least partially receive the user's nose and mouth (see FIG. 1). In this embodiment, the opening 18 may have a length of between about 1.0 to 3.0 inches and a width of between about 1.0 to 1.75 inches, and the body 12 may have a length of between about 4.5 to 7.5 inches and a width of between about 4.5 to 6.5 inches. If the liner 10 is to be used with a nasal CPAP mask, the opening 18 may be sized to at least partially receive the user's nose (see FIG. 2). In this embodiment, the opening 18 may have a length of between about 1.25 to 1.75 inches and a width of between about 0.75 to 1.5 inches, and the body 12 may have a length of between about 3.0 to 4.0 inches and a width of between about 3.0 to 5.0 inches. If the liner 10 is to be used with a partial-face CPAP mask, the opening 18 may be sized to at least partially receive the user's mouth (see FIG. 3). In this embodiment, the opening 18 may have a length of between about 0.5 and 1.0 inches and a width of between about 1.75 and 2.25 inches, and the body 12 may have a length of between about 2.5 to 4.0 inches and a width of between about 4.25 and 6.0 inches. It is understood, however, that these embodiments are not intended to be limiting, and the liner 10 could be configured to fit any size or shape of CPAP mask M.

Figure 4:
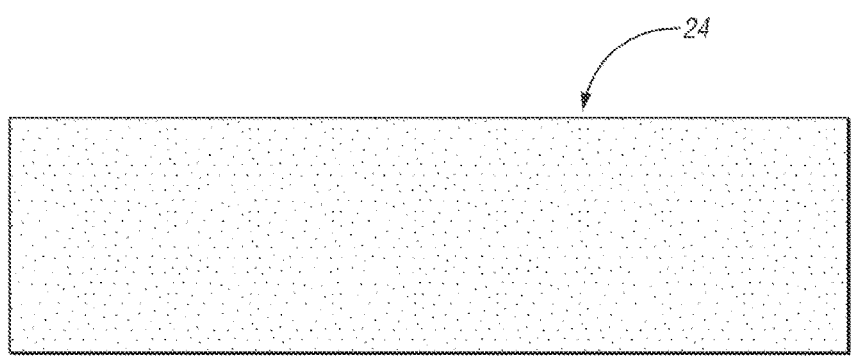
FIG. 4 is a top plan view of a forehead liner according to an aspect of the present invention.

Turning to FIG. 4, a forehead liner 24 may also be provided to interface with a forehead stabilizer portion S of a respiratory mask M (see FIG. 5) to create a two-piece liner system in accordance with an embodiment. The forehead liner 24 is configured to be releasably held by the forehead stabilizer portion S and the user's face, and may have an area at least as large as an area of the forehead stabilizer portion S. The forehead liner 24 may have a generally rectangular shape, and may comprise a single or multi-layer material such as, but not limited to, cotton. In one embodiment, the forehead liner 24 comprises three layers of an absorbent material. The forehead liner 24 may have a shape that is generally similar to the shape of the forehead stabilizer portion S, and may extend beyond the perimeter of the forehead stabilizer portion S by between about 0.5 to 0.75 inches, although it is understood that the forehead liner 24 is not limited to this configuration. Liner 10 and forehead liner 24 may be used together, but may also be used separately as desired by a user.

Figure 6:
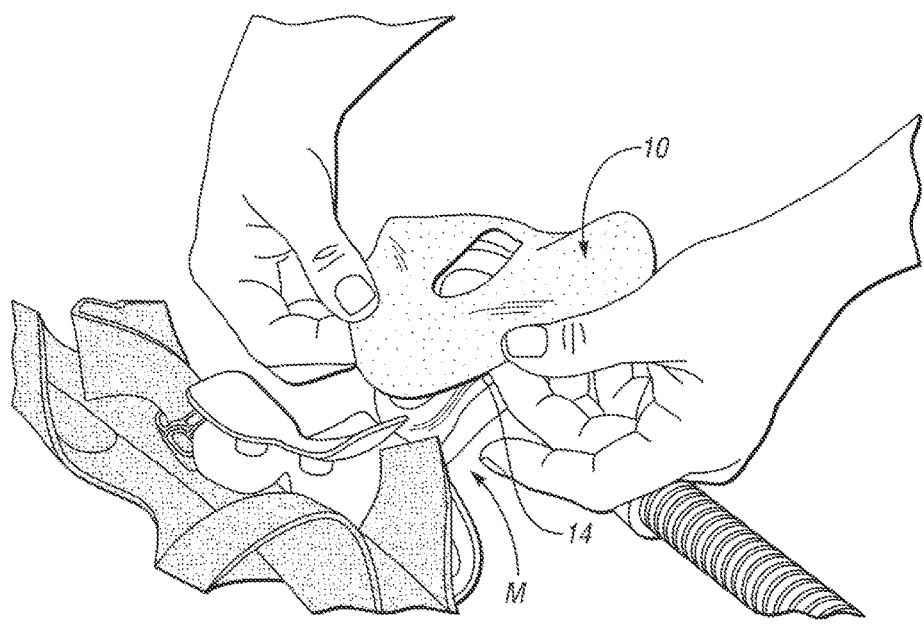
FIG. 6 is an illustration of placement of a liner in accordance with an embodiment on the face-engaging portion of a respiratory mask.
Figure 7:
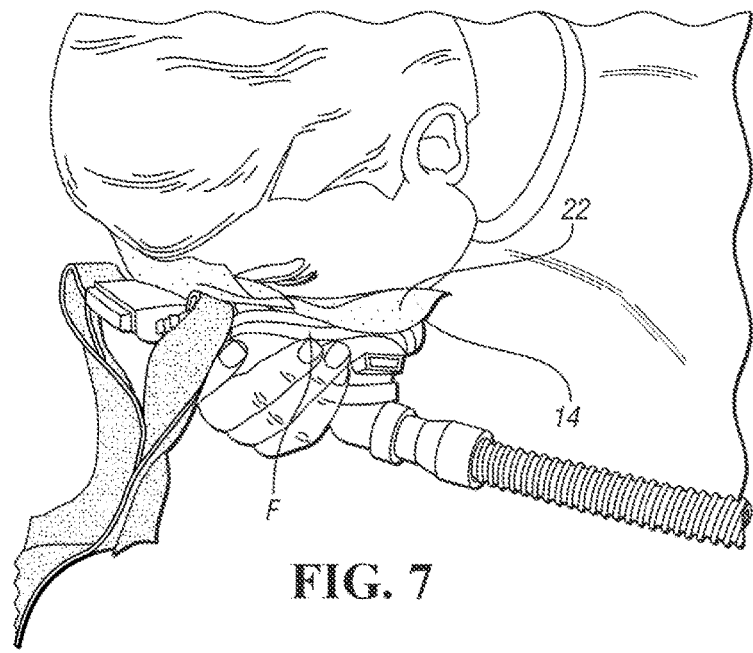
FIG. 7 is an illustration of a user engaging the liner placed on the mask, fitting her nose and mouth into the liner opening.
Figure 8:
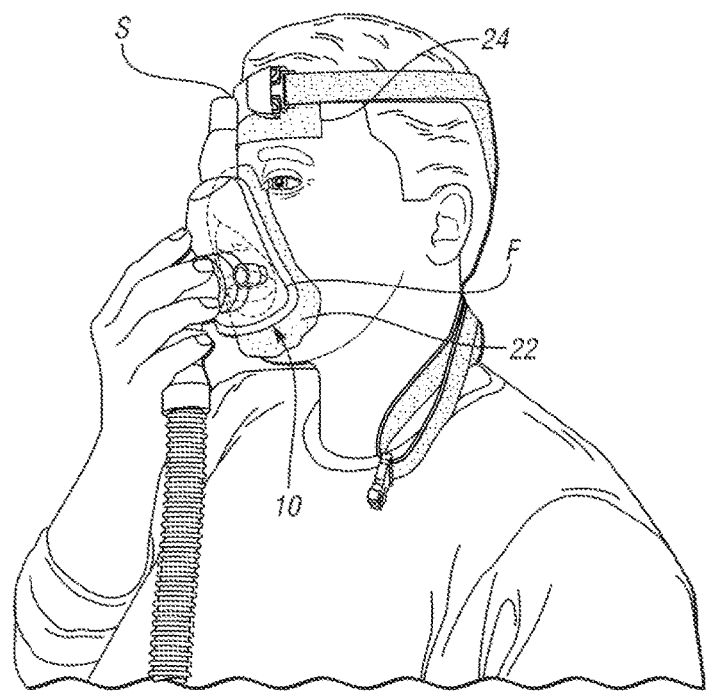
FIG. 8 is an illustration of a user returning her head to an upright position while holding the mask and liner against her face.
Figure 9:
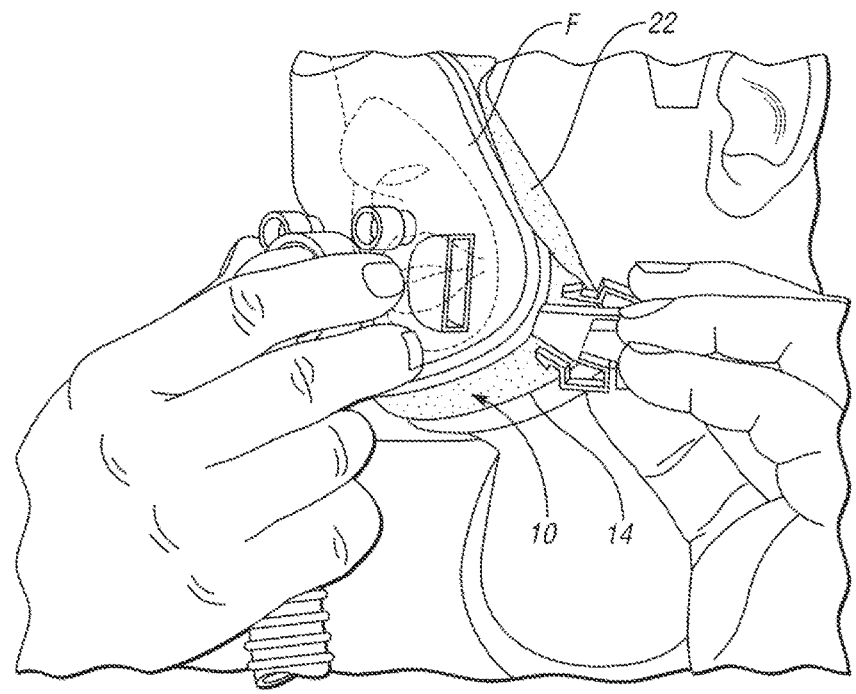
FIG. 9 is an illustration of a user attaching the mask straps.
Figure 10:
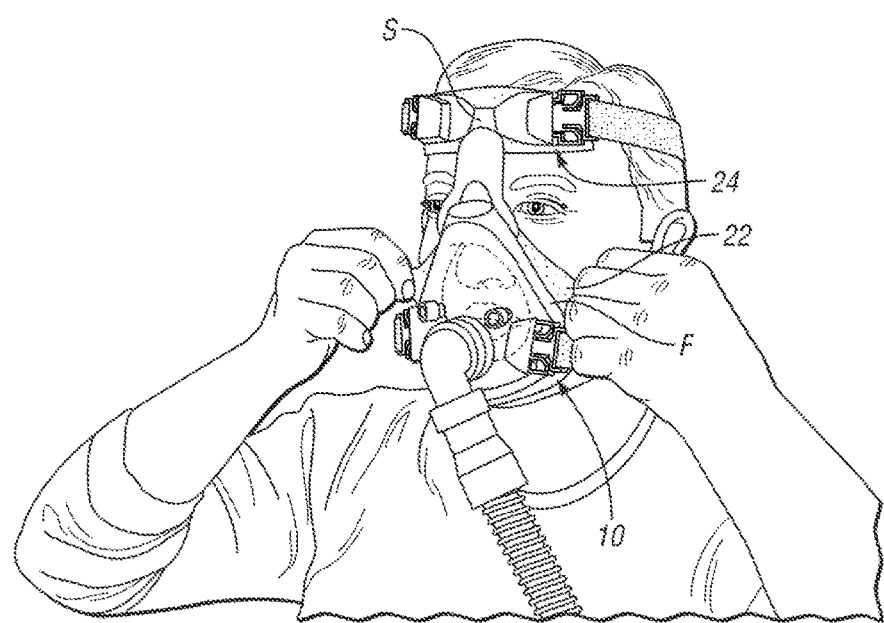
FIG. 10 is an illustration of a user adjusting the positioning of the liner by pulling on the second portion of the liner body protruding beyond the perimeter of the face-engaging portion.

Referring now to FIGS. 6-10, a method of using the liner 10 according to an embodiment will be described. As shown in FIG. 6, the liner 10 may be placed over the face-engaging portion F such that the outer edge 14 extends beyond and is spaced apart from the face-engaging portion F. Although not shown in this figure, the forehead liner 24 can also be placed on the forehead stabilizer portion S if desired. The user may then lean his/her face downward toward the mask M, fitting his/her nose and/or mouth (as applicable) into the opening 18 as depicted in FIG. 7. Next, the user may press his/her face against the liner 10 and mask M while returning his/her head to a normal upright position as shown in FIG. 8. As illustrated in FIG. 9, the user may then snap the mask fasteners into place and adjust their tightness to secure the mask M. Securing the mask M releasably holds the liner 10 between the face-engaging portion F and a user's face, such that the liner 10 regulates air flow and reduces air leaks between the face-engaging portion F and the user's face. Lastly, with reference to FIG. 10, the liner 10 may be adjusted, such as around the nose and mouth, by pulling outward on the protruding extending portion 22, thereby providing a customized fit for a particular user. Of course, it is understood that variations on the above-described use of liner 10 and forehead liner 24 are fully contemplated.

Figure 11:
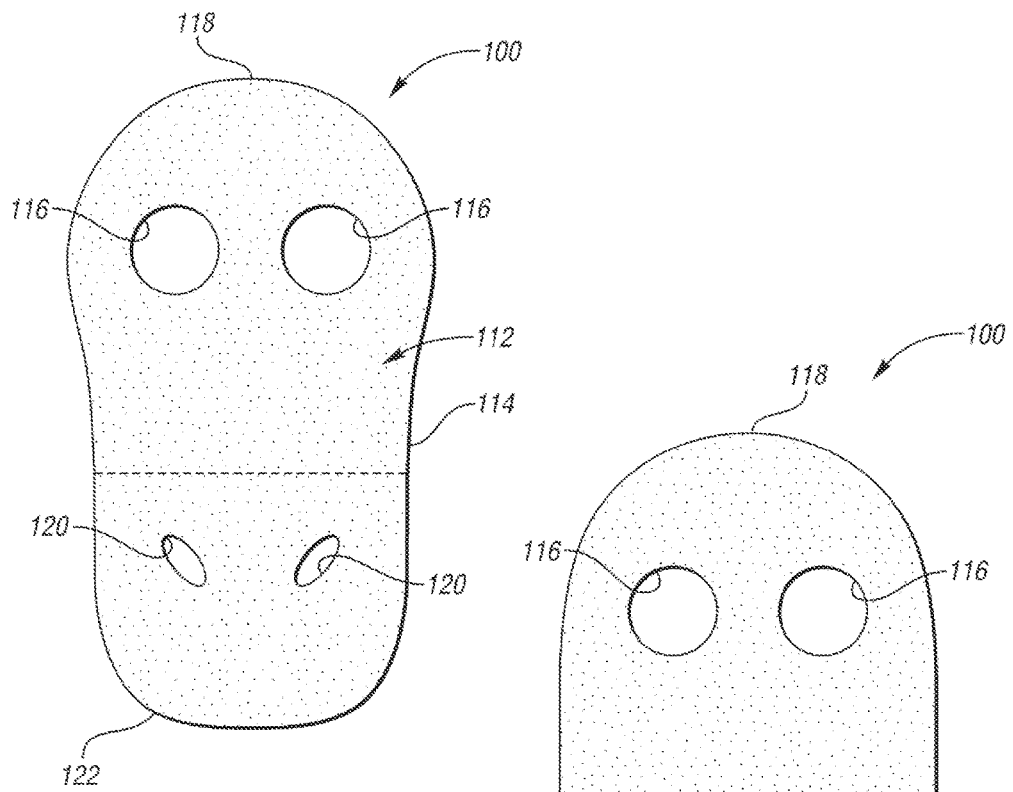
FIG. 11 is a top plan view of a liner according to an embodiment, such as for use with a nasal pillow mask.
Figure 14:
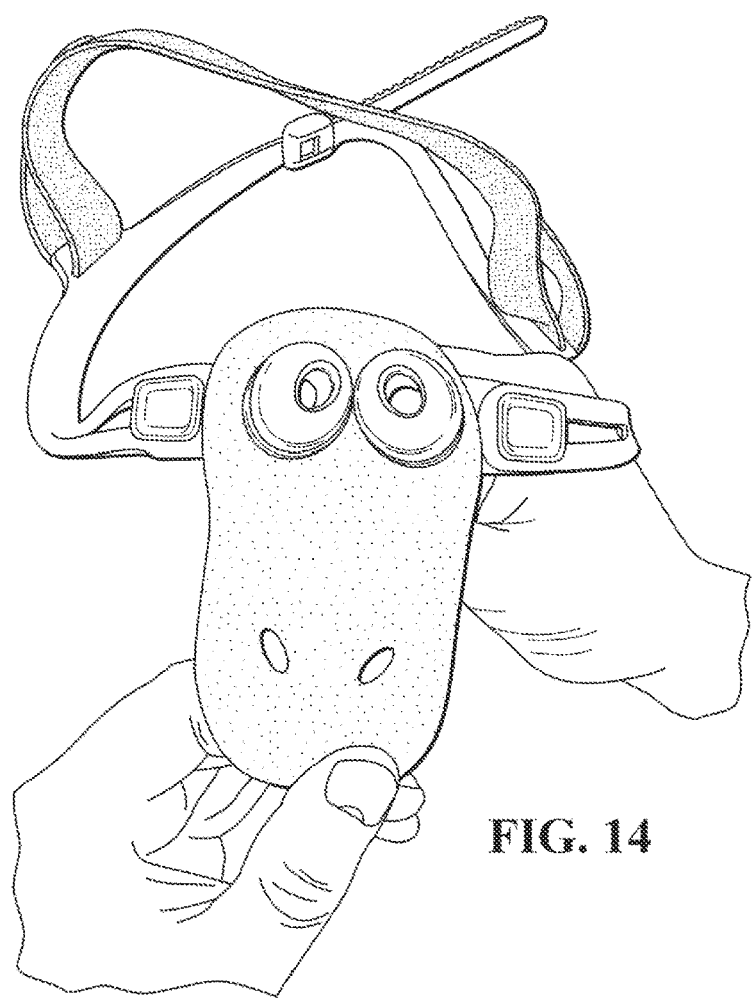
FIG. 14 is a photograph of placement of a first pair of apertures of a liner as in FIG. 11 in accordance with an embodiment over the nasal pillows of a nasal pillow mask.

In another embodiment, a liner 100 as illustrated in FIG. 11 is provided which includes a plurality of apertures, such as for use with a nasal pillow mask, as shown in FIG. 14, for example. The liner 100 includes a body 112 having an outer edge 114, a first pair of apertures 116 which may be adjacent a first end 118 of the liner 100, and a second pair of apertures 120 which may be adjacent a second end 122 of the liner 100. The body 112 may be generally oval-shaped, elliptical, round, triangular, or rectangular, or have any other shape appropriate for use with a respiratory mask, and is not limited to the shape depicted herein. The first pair of apertures 116 are sized to be placed over the nasal pillows of a nasal pillow mask for maintaining proper position of the liner 100 and, in a non-limiting example, may be approximately 0.5 to 1.0 inches in diameter. The second pair of apertures 120 are sized to lay on top of the nasal pillows to provide comfort to a user's nostrils and allow air to flow through the nasal pillows and into the user's nostrils. The second pair of apertures 120 may be generally circular or oval-shaped as shown, but are not intended to be limited to these shapes.

In another embodiment, which may be for use with a nasal pillow mask, the liner 100 may include an additional aperture 124 sized for placement over the hose connection of the mask for possible added stability. In this embodiment, the second pair of apertures 120 may be disposed more centrally along the length of the liner 100.

Figure 13:
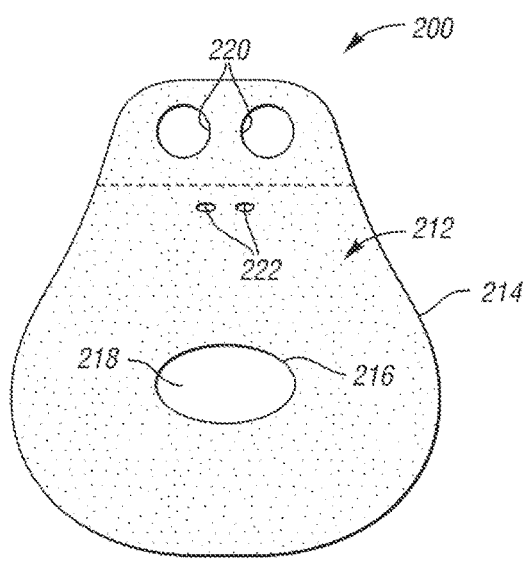
FIG. 13 is a top plan view of a liner according to an embodiment, such as for use with a hybrid nasal pillow/partial face mask.
Figure 26:
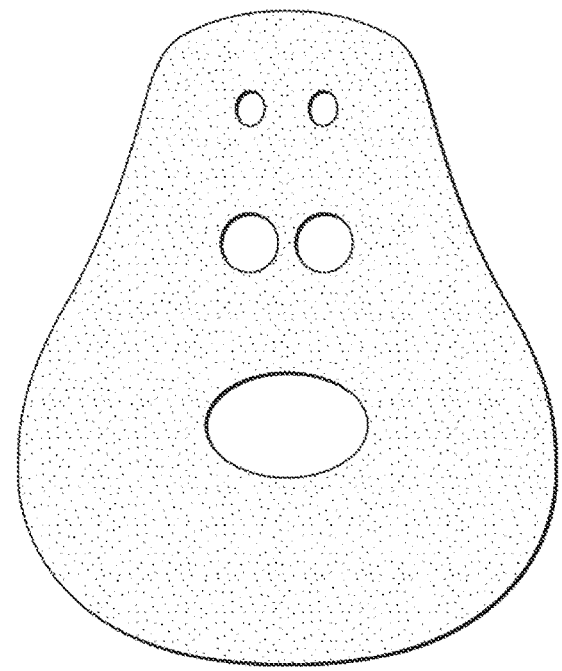
FIG. 26 is a top plan view of a liner according to an embodiment, such as for use with a hybrid nasal pillow/partial face mask.

For a hybrid face-nasal pillow mask, the embodiment of FIG. 13 may be utilized. The liner 200 includes a body 212 having an outer edge 214, an inner edge 216, and an opening 218 bounded by the inner edge 216. The body 212 may be generally oval-shaped, elliptical, round, triangular, or rectangular, or have any other shape appropriate for use with a respiratory mask, and is not limited to the shape depicted herein. The opening 218 is configured to at least partially receive the mouth, allowing air flow from an air source to be received by the user through the mask. The opening 218 may be generally elliptical or oval-shaped as shown, but is not intended to be limited to these shapes. The liner 200 further includes a first pair of apertures 220, which may be adjacent an end of the liner 200, and a second pair of apertures 222 set inward from the first pair of apertures 220. The first pair of apertures 220 are sized to be placed over the nasal pillows for maintaining proper position of the liner 100 and, in a non-limiting example, may be approximately 0.5 to 1.0 inches in diameter. The second pair of apertures 222 are sized to lay on top of the nasal pillows to provide comfort for a user's nostrils and allow air to flow through the nasal pillows and into the user's nostrils. The second pair of apertures 222 may be generally circular or oval-shaped as shown, but are not intended to be limited to these shapes. FIG. 26 illustrated another, related embodiment, wherein the description of FIG. 13 may also be applicable.

Figure 12:
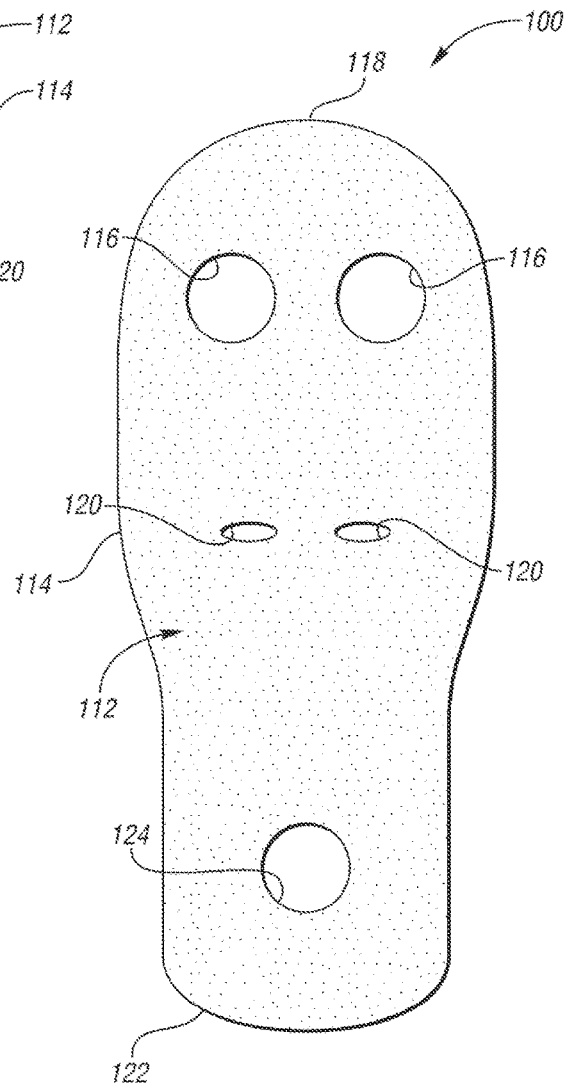
FIG. 12 is a top plan view of a liner according to another embodiment for use with a nasal pillow mask.

In the embodiment of FIG. 11, the body 112 may have a length of between about 4.0 to 5.0 inches and a width of between about 2.0 to 3.0 inches. In the embodiment of FIG. 12, the length of the body 112 may be between 6.0 and 7.0 inches and the width of the body may be between about 2.0 to 3.0 inches. In the embodiment of FIG. 13, the opening 218 may have a length of between about 1.0 to 3.0 inches and a width of between about 1.0 to 1.75 inches, and the body 212 may have a length of between about 6.0 to 7.0 inches. The body 212 may have a width of between about 5.0 to 6.0 inches at a bottom portion thereof adjacent the opening 218 and between about 2.5 to 3.5 inches at a top portion thereof adjacent the first pair of apertures 220. It is understood, however, that these embodiments are not intended to be limiting, and the liners 100, 200 could be configured to fit any size or shape of CPAP mask.

In use, the liners 100, 200 may be positioned between and held in place by the respiratory mask and the face of a user in order to absorb moisture, maintain proper positioning of the mask, and greatly reduce or eliminate air from leaking between the mask and the user's face. A perimeter of the liner outer edge 114, 214, which may be continuous or discontinuous, is larger than a perimeter of the face-engaging portion (including nasal pillows) of the mask, wherein the liners 100, 200 are configured to be releasably held between the mask and a user's face such that the outer edge 114, 214 extends beyond the mask face-engaging portion around at least part of its perimeter. As such, the body 112, 212 has an extending portion outward of the perimeter of the face-engaging portion. By allowing the outer edge 114, 214 of the liner 100, 200 to loosely protrude beyond the mask, the extending portion is configured to be in non-adhering communication with a user's face and serves to reduce air leaks from the perimeter of the mask by acting as a baffle to regulate, limit, or diffuse air flow between the mask and the skin, thus also stopping any resulting squealing-type noises created by such air leaks. It is understood that the other features described above with reference to liner 10 may also be applicable to liners 100, 200.

Figure 15:
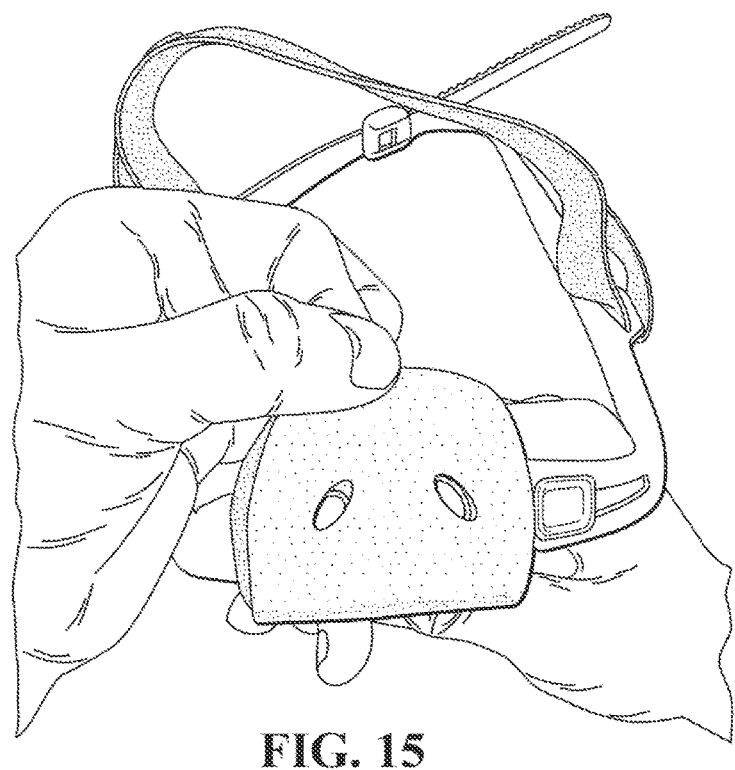
FIG. 15 is a photograph illustrating a user folding the liner of FIG. 11 so that a second pair of apertures is aligned with the nasal pillows.
Figure 16:
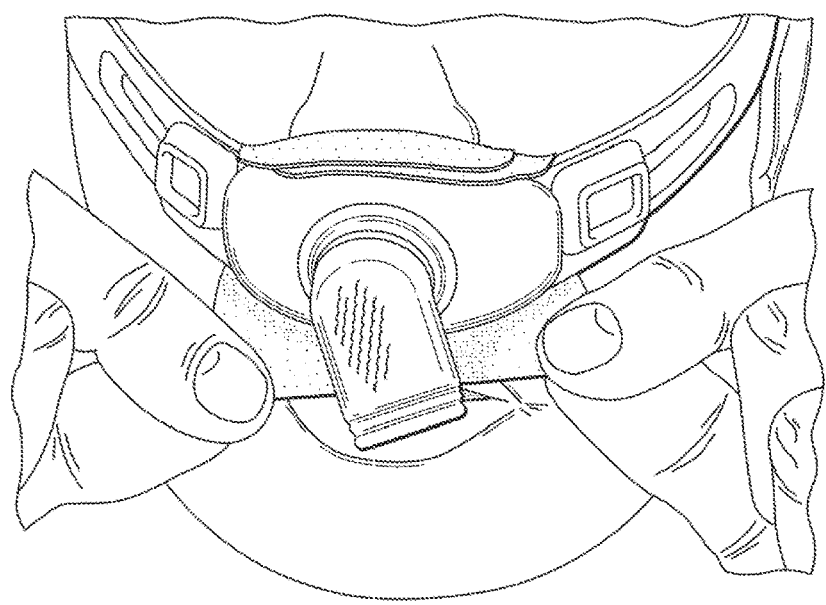
FIG. 16 is a photograph illustrating a user adjusting the positioning of the liner of FIG. 11 by pulling on the portion of the liner body protruding beyond the perimeter of the nasal pillow mask.

With reference to FIGS. 14-16, a method of using liner 100 according to an embodiment is described below. FIG. 14 illustrates placement of the first pair of apertures 116 over the nasal pillows of a nasal pillow mask. FIG. 15 illustrates a user folding the liner 100 so that the second pair of apertures 120 is aligned with the nasal pillows, wherein in one embodiment the fold may occur approximately at a location as indicated by dashed lines in FIG. 11. The user may then place his/her nostrils over the top of the nasal pillows with the liner 100 in between, and proceed to secure the mask. FIG. 16 illustrates a user adjusting the positioning of the liner 100 if desired by pulling on the extending portion of the liner body 112 protruding beyond the perimeter of the nasal pillow mask.

Figure 17:
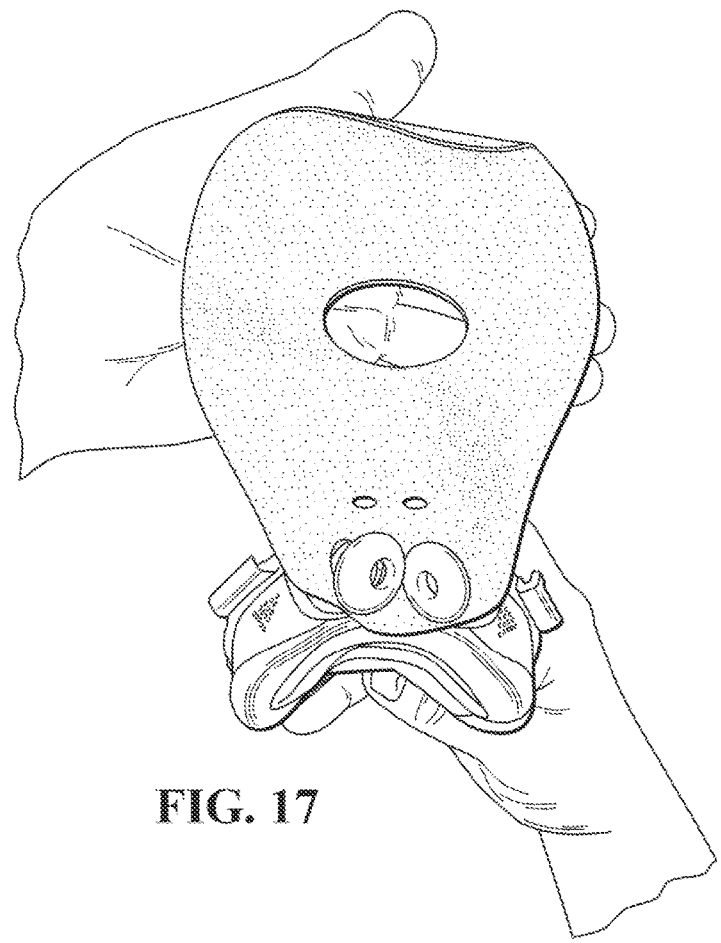
FIG. 17 is a photograph of placement of a first pair of apertures of a liner as in FIG. 13 in accordance with an embodiment over the nasal pillows of a hybrid nasal pillow/partial face mask.
Figure 18:
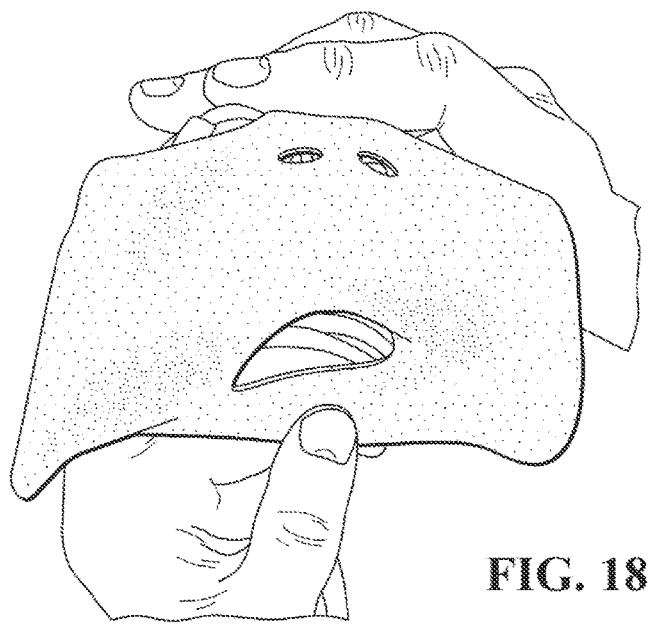
FIG. 18 is a photograph illustrating a user folding the liner of FIG. 13 so that a second pair of apertures is aligned with the nasal pillows.
Figure 19:
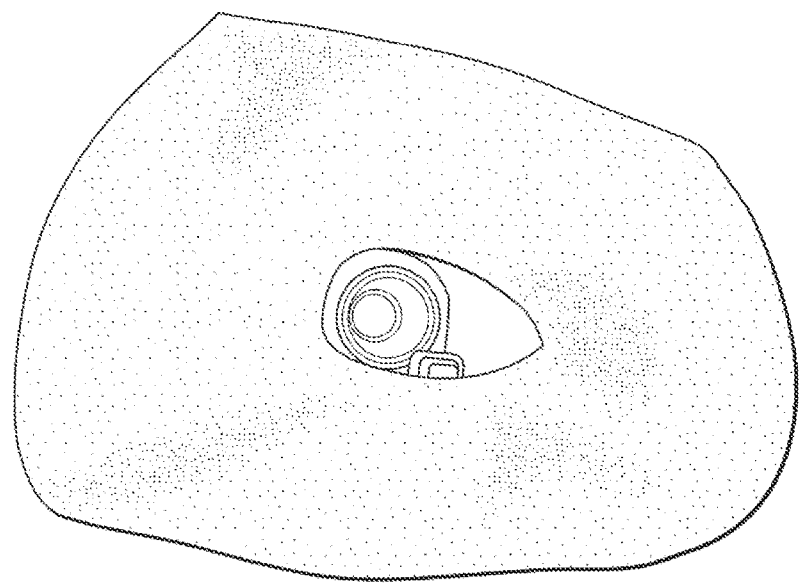
FIG. 19 is a photograph illustrating alignment of the opening of the liner of FIG. 13 with the face-engaging portion of the hybrid mask.
Figure 20:
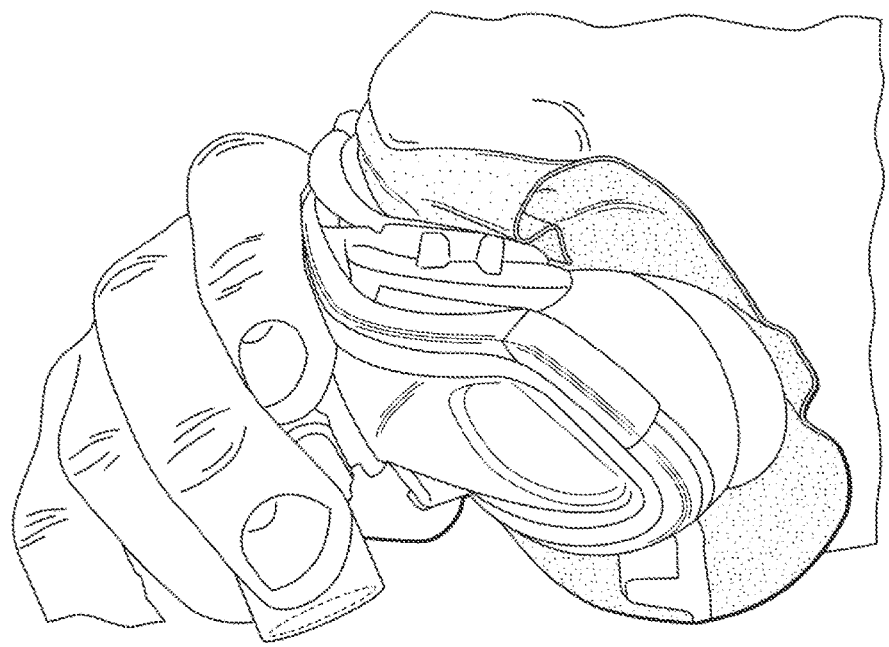
FIG. 20 is a photograph illustrating a user engaging the liner of FIG. 13 placed on the hybrid mask, fitting his nose to the nasal pillows and mouth into the liner opening.

With reference to FIGS. 17-20, a method of using liner 200 according to an embodiment is described below. FIG. 17 illustrates placement of the first pair of apertures 220 over the nasal pillows of a hybrid nasal pillow/partial face mask. FIG. 18 illustrates a user folding the liner 200 so that the second pair of apertures 222 is aligned with the nasal pillows, wherein in one embodiment the fold may occur approximately at a location as indicated by dashed lines in FIG. 13. FIG. 19 illustrates alignment of the opening 218 with the mouthpiece and face-engaging portion of the hybrid mask. FIG. 20 illustrates a user engaging the liner 200 placed on the hybrid mask, fitting his nostrils to the nasal pillows and mouth into the liner opening 218, after which the user can proceed to secure the mask. The liner 200 may then be adjusted, such as around the nose and mouth, by pulling outward on the protruding extending portion, thereby providing a customized fit for a particular user. Of course, it is understood that variations on the above-described use of liners 100, 200 are fully contemplated.

Figure 21:
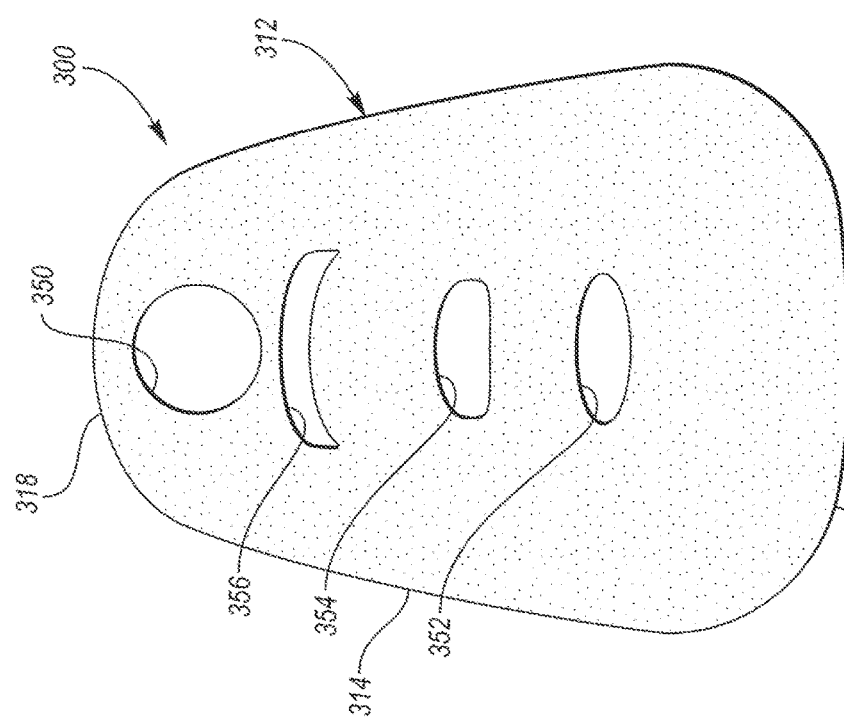
FIG. 21 is a top plan view of a liner according to another embodiment for use with a respiratory mask having a detachable frame.
Figure 23:
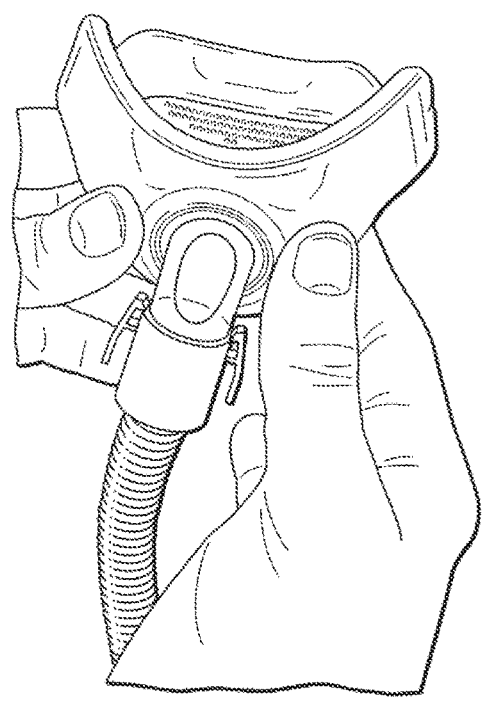
FIG. 23 is a photograph of an exemplary respiratory mask having a detachable frame.

In another embodiment, a liner 300 as illustrated in FIG. 21 is provided which includes a plurality of apertures, such as for use with a respiratory mask wherein the frame portion is detachable from the cushion portion, as shown in FIG. 23, for example. The liner 300 includes a body 312 having an outer edge 314, and a hose aperture 350 which may be adjacent a first end 318 of the liner 300 and sized for placement over the hose connector of the mask. The liner 300 includes a mouth aperture 352 which may be adjacent a second end 322 of the liner 300 and configured for placement over the mouth opening of the mask to allow air to flow into the user's mouth, and a nasal aperture 354 set farther inward from the second end 322 compared to the mouth aperture 352 and configured for placement over the nasal opening of the mask to allow air to flow into the user's nostrils. In an alternative embodiment, it is contemplated that a combined mouth and nasal opening could be provided in the mask, such that mouth aperture 352 and nasal aperture 354 could be formed as a single aperture. In addition, the liner 300 may include an export aperture 356 disposed between the hose aperture 350 and the nasal aperture 354, wherein the export aperture 356 is configured for placement over an export air portion of the mask, such as the plurality of air holes illustrated in FIG. 23.

Figure 22:
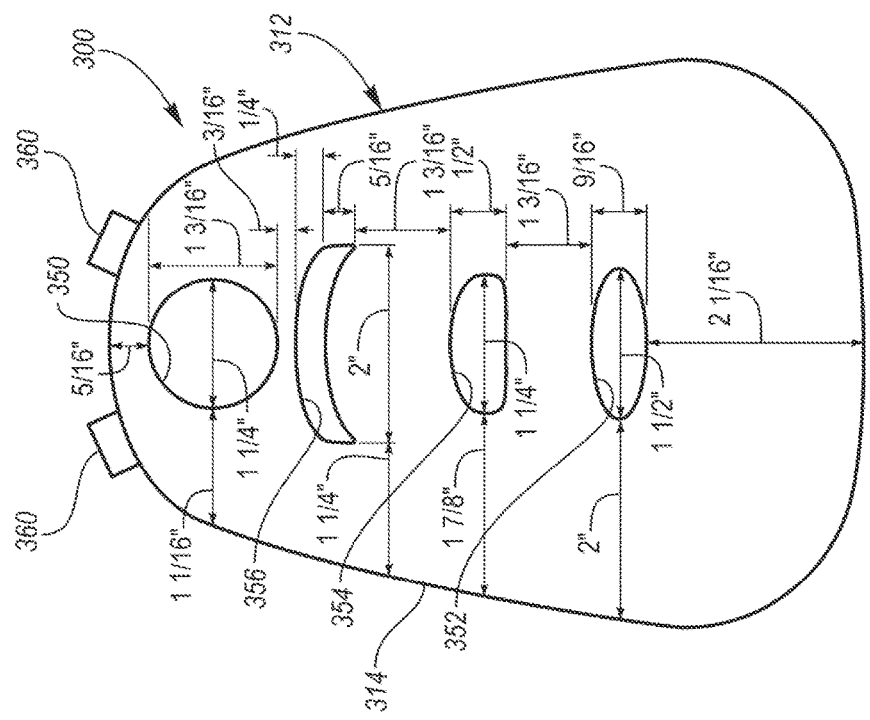
FIG. 22 is a top plan of the liner of FIG. 21 annotated with exemplary, non-limiting dimensions for construction.

The body 312 may be generally oval-shaped, elliptical, round, triangular, or rectangular, or have any other shape appropriate for use with a respiratory mask, and is not limited to the shape depicted herein. The apertures 350, 352, 354 and 356 may be generally circular or elongate or oval-shaped as shown, but are not intended to be limited to these shapes. With reference to FIG. 22, exemplary dimensions for the configuration of liner 300 are shown. It is understood, however, that these dimensions are not intended to be limiting, and the liner 300 could be configured to fit any size or shape of CPAP mask.

In use, the liner 300 may be positioned between and held in place by the respiratory mask and the face of a user in order to absorb moisture, maintain proper positioning of the mask, and greatly reduce or eliminate air from leaking between the mask and the user's face. A perimeter of the liner outer edge 314, which may be continuous or discontinuous, is larger than a perimeter of the face-engaging portion of the mask, wherein the liner 300 is configured to be releasably held between the mask and a user's face such that the outer edge 314 extends beyond the mask face-engaging portion around at least part of its perimeter. As such, the body 312 has an extending portion outward of the perimeter of the face-engaging portion. By allowing the outer edge 314 of the liner 300 to loosely protrude beyond the mask, the extending portion is configured to be in non-adhering communication with a user's face and serves to reduce air leaks from the perimeter of the mask by acting as a baffle to regulate, limit, or diffuse air flow between the mask and the skin, thus also stopping any resulting squealing-type noises created by such air leaks. It is understood that the other features described above with reference to liners 10, 100 and 200 may also be applicable to liner 300.

Figure 24:
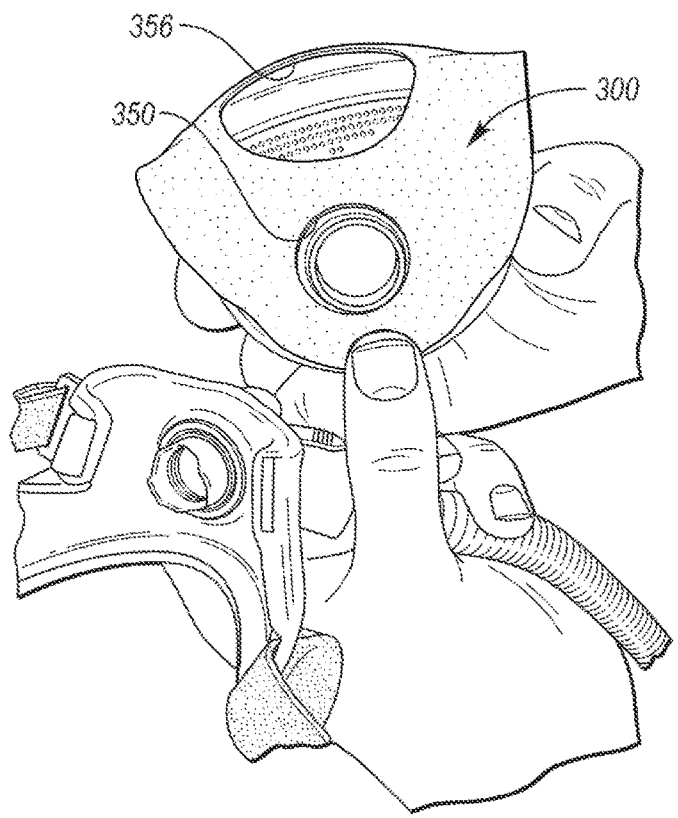
FIG. 24 is a photograph of the liner of FIG. 21 placed on the mask of FIG. 23 with the frame detached.
Figure 25:
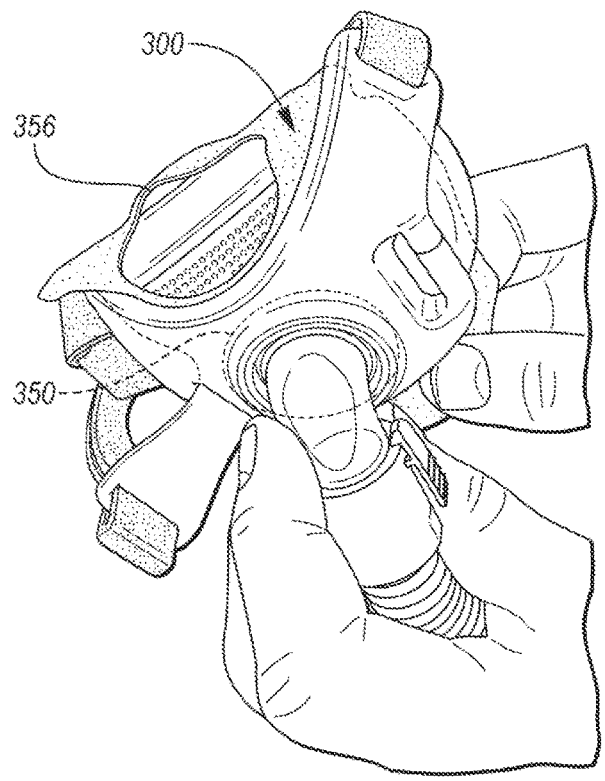
FIG. 25 is a photograph of the liner of FIG. 21 placed on the mask of FIG. 23 with the frame attached.

With reference to FIGS. 24-25, a method of using liner 300 according to an embodiment is described below. FIG. 24 illustrates placement of the liner 300 with the frame detached such that the hose aperture 350 is received over the hose connector of the mask, the export aperture 356 is aligned with an export air portion of the mask, the nasal aperture 354 is aligned with a nasal opening of the mask, and the mouth aperture 352 is aligned with a mouth opening of the mask. The user may then align his/her nostrils with the nasal aperture 354 and his/her mouth with the mouth aperture 352, and proceed to secure the mask. FIG. 24 illustrates the frame attached to the mask with the liner 300 in place. A user may adjust the positioning of the liner 300 if desired by pulling outward on the extending portion of the liner body 312 protruding beyond the perimeter of the respiratory mask, thereby providing a customized fit for a particular user. In one embodiment (FIG. 22), at least one adhesive tab 360 may be provided at liner first end 318 for securing the liner 300 to the mask, such as near the hose connection, thus helping to ensure that export aperture 356 does not in any way obstruct the export air portion of the mask when the liner 300 is in use with the mask. Tabs 360 do not change the configuration of the outer edge 314 of the liner 300 in the area of the nasal and mouth openings of the mask, where the outer edge 314 still loosely protrudes beyond the mask as described above. Of course, it is understood that variations on the above-described use of liner 300 are fully contemplated.

Copper is a natural mineral having human nutritional benefit. Copper is also known to provide antimicrobial and potential wound healing properties. In one embodiment, the liners 10, 100, 200, 300 described herein may be manufactured with a copper or copper oxide material, such as CUPRON®.

CPAP therapy is the most widely used method for treating sleep apnea, but it is only successful when the equipment fits and works properly and allows the user to stay asleep and experience deep-sleep, rapid eye movement (REM) cycles, the sleep cycle in which the most beneficial rest takes place. The liners 10, 100, 200, 300 may facilitate a more comfortable and effective CPAP therapy by contributing to a good fit of the CPAP mask M, providing comfort to the user, and reducing or eliminating air leaks, thus resulting in less disruption of sleep.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A liner for use with a respiratory mask having a frame portion which is detachable from a cushion portion, the liner comprising:
    a body constructed from an absorbent material, the body having a first end and a second end, the body including a hose aperture adjacent the first end and sized for placement over a hose connector of the respiratory mask, and a mouth aperture adjacent the second end for placement over a mouth opening of the mask to allow air to flow into a user's mouth, wherein the liner is treated with a copper or copper oxide material.

2. The liner of claim 1, wherein the body further includes a nasal aperture set farther inward from the second end compared to the mouth aperture for placement over a nasal opening of the mask to allow air to flow into the user's nostrils.

3. The liner of claim 2, wherein the mouth and nasal apertures are generally oval-shaped.

4. The liner of claim 2, wherein the mouth aperture and the nasal aperture are formed as a single combined aperture.

5. The liner of claim 1, wherein the body further includes an export aperture disposed between the hose aperture and the mouth aperture, wherein the export aperture is placed over an export air portion of the mask.

6. The liner of claim 1, wherein the body comprises a single layer of material.

7. The liner of claim 1, wherein the material is stretchable.

8. The liner of claim 1, wherein the liner is releasably held between the mask and the user's face.

9. A liner for use with a respiratory mask having a frame portion which is detachable from a cushion portion, the liner comprising:
    a body constructed from an absorbent material, the body having a first end and a second end, the body including a hose aperture adjacent the first end and sized for placement over a hose connector of the respiratory mask, a mouth aperture adjacent the second end for placement over a mouth opening of the mask to allow air to flow into a user's mouth, and a separate nasal aperture set farther inward from the second end compared to the mouth aperture for placement over a nasal opening of the mask to allow air to flow into the user's nostrils.

10. The liner of claim 9, wherein the body further includes an export aperture disposed between the hose aperture and the nasal aperture, wherein the export aperture is placed over an export air portion of the mask.

11. The liner of claim 9, wherein the material is stretchable.

12. The liner of claim 9, wherein the liner is treated with a copper or copper oxide material.

13. The liner of claim 9, wherein the liner is releasably held between the mask and the user's face.

14. A liner for use with a respiratory mask having a frame portion which is detachable from a cushion portion, the liner comprising:
    a body constructed from an absorbent material, the body having a first end and a second end, the body including a hose aperture adjacent the first end and sized for placement over a hose connector of the respiratory mask, a mouth aperture adjacent the second end for placement over a mouth opening of the mask to allow air to flow into a user's mouth, and an export aperture disposed between the hose aperture and the mouth aperture, wherein the export aperture is placed over an export air portion of the mask.

15. The liner of claim 14, wherein the body further includes a nasal aperture disposed between the mouth aperture and the export aperture for placement over a nasal opening of the mask to allow air to flow into the user's nostrils.

16. The liner of claim 15, wherein the mouth aperture and the nasal aperture are formed as a single combined aperture.

17. The liner of claim 14, wherein the material is stretchable.

18. The liner of claim 14, wherein the liner is treated with a copper or copper oxide material.

19. The liner of claim 14, wherein the liner is releasably held between the mask and the user's face.

* * * * *